United States Patent [19]

Ramprasad et al.

[11] Patent Number: 5,294,418
[45] Date of Patent: * Mar. 15, 1994

[54] PROCESS FOR REVERSIBLY BINDING OXYGEN

[75] Inventors: Dorai Ramprasad, Allentown, Pa.; Ingrid K. Meier, Asbury, N.J.; Ronald M. Pearlstein, Macungie; Guido P. Pez, Allentown, both of Pa.

[73] Assignee: Air Products and Chemicals, Inc., Allentown, Pa.

[*] Notice: The portion of the term of this patent subsequent to Aug. 25, 2009 has been disclaimed.

[21] Appl. No.: 960,497

[22] Filed: Oct. 13, 1992

Related U.S. Application Data

[63] Continuation-in-part of Ser. No. 890,065, May 27, 1992, Pat. No. 5,208,335, which is a continuation-in-part of Ser. No. 672,711, Mar. 19, 1991, Pat. No. 5,126,466.

[51] Int. Cl.$^5$ .............................................. C01B 13/00
[52] U.S. Cl. .................................... 423/219; 423/364
[58] Field of Search ............................ 423/364, 219

[56] References Cited

U.S. PATENT DOCUMENTS

| | | | |
|---|---|---|---|
| 3,530,004 | 9/1970 | Coffield | 423/364 |
| 3,980,763 | 9/1976 | Mullhaupt | 423/579 |
| 4,251,452 | 2/1981 | McAuliffe et al. | 260/429 |
| 4,477,418 | 10/1984 | Mullhaupt et al. | 423/219 |
| 4,830,999 | 5/1989 | Drazo et al. | 502/74 |
| 5,126,466 | 6/1992 | Ramprasad et al. | 55/74 |
| 5,141,725 | 8/1992 | Ramprasad et al. | 423/219 |

FOREIGN PATENT DOCUMENTS 0090444 10/1983 European Pat. Off. ............ 423/364

OTHER PUBLICATIONS

J. H. Hildebrand, "The Thermal Dissociation of Barium Peroxide", J. Amer. Chem. Soc., 34, p. 246 (1912).

R. S. Drago, et al, "Entrapment of an Anionic, Stable, Moisture-Resistant Oxygen Carrier in Zeolite Y", J. Amer. Chem. Soc., 110, p. 304 (1988).

G. A. Kozlov et al. "Structure and Properties of the Products of Reaction Between Molecular Oxygen and New Salts of Pentacyanocobaltate (II) Anion," Teoreticheskaya Eksperimental Naya Khimiya, 1981, vol. 17, No. 5, pp. 686–691.

S. Imamura, et al, "Separation of Oxygen from Air by [Co$^{II}$(bpy)(terpy)]$^{24}$Complexes in Zeolite Y", Tangmiur, (1985) 1, p. 326-330.

R. J. Taylor, et al, "Characterization of a Cobalt (II) Cyanide Complex Inside Zeolite Y that Reversibly Binds Oxygen", J. Amer. Chem. Soc., III, 6610, (1989).

S. J. Carter, et al, "Cobalt (II) Cyanides in Aprotic Media:Effect of Varying Counterion and Solvent", Inorg. Chem. 25, pp. 2888–2894 (1986).

S. J. Carter, "Synthesis, Characterization and Reactions of New Organocyanocobaltates", Thesis Brandeis University, 1988.

S. J. Carter, et al, "Isolation and Characterization of (PNP)$_2$ Co(CN)$_4$; an Unusual Square-Planar Cobalt (II) Complex", J. Am. Chem. Soc., 106 pp. 4265–4266 (1984).

Primary Examiner—Wayne Langel
Attorney, Agent, or Firm—Mark L. Rodgers; James C. Simmons; William F. Marsh

[57] ABSTRACT

High capacity solid state compositions comprising cyanocobaltate complexes have been developed which are capable of reversibly chemically binding oxygen to selectively remove oxygen from an oxygen-containing fluid stream. The cyanocobaltate complexes which make up the compositions comprise a cobalt (II)-containing anion having from 3 to 5 cyanide ligands wherein at least one cyanide stretching mode, as measured by infrared spectroscopy, is between 2074 cm$^{-1}$ and 2140 cm$^{-1}$. Additionally, these complexes have a charge-balancing cation having a molecular volume in excess of 40Å$^3$.

18 Claims, No Drawings

PROCESS FOR REVERSIBLY BINDING OXYGEN

CROSS REFERENCE TO RELATED APPLICATION

This is a continuation-in-part of copending application Ser. No. 07/890,065 filed 27 May 1992, U.S. Pat. No. 5,208,335, which is a continuation-in-part of application Ser. No. 07/672,711 filed 19 March 1991, U.S. Pat. No. 5,126,466, which is hereby incorporated by reference.

TECHNICAL FIELD

The present invention relates to materials which are useful for the selective separation and recovery of oxygen from air or other oxygen-containing fluid streams.

BACKGROUND OF THE INVENTION

Gas separations may be carried out by a number of methods including distillation at cryogenic temperatures, the use of permselective membranes and by processes that utilize compositions that can reversibly and selectively sorb a component of the gas mixture. For sorption-based separation of air, current commercial technologies utilize zeolite molecular sieves as $N_2$-selective adsorbents and carbon molecular sieve (CMS) materials as $O_2$-selective adsorbents. These technologies, which are usually employed for the production of enriched nitrogen or oxygen, (rather than very high purity $N_2$ or $O_2$) have several inherent limitations which restrict their competitiveness against the cryogenic and membrane separation methods.

Synthetic zeolites reversibly adsorb nitrogen in preference to oxygen. When used for instance in a pressure-swing adsorption (PSA) process for the separation of air, the zeolite bed selectively takes up the nitrogen which is recovered by de-pressurization or evacuation of the bed. The drawback in this separation method is that it is performed inefficiently by adsorbing nitrogen which is the major component of air.

The potential advantages of selective oxygen sorbents have long been recognized and there has been much research effort directed at the synthesis of suitable materials. At the present time carbon molecular sieve (CMS) kinetically oxygen selective adsorbents are used in PSA air separation processes for the production of either enriched $N_2$ or $O_2$. Several factors limit the productivity and hence the cost-effectiveness of this technology. Even the most effective current CMS sorbents have a poor working $O_2/N_2$ selectivity in the PSA process. The necessarily short cycle times of the PSA process and the limiting oxygen adsorption kinetics lead to a poor utilization of the adsorption bed.

U.S. Pat. No. 4,477,418 discloses solid state transition metal hexacyano compounds (cyanometallates) defined as $M_x[M'(CN)_6]_y$ where M=Sc, Mn, Fe, Co, Ni etc and M' is strictly Cr, Mn, Fe, Co which are selective oxygen sorbents which are taught to be useful in processes for the separation of oxygen. The hexacyanometallate solids can be microporous, containing very small voids within their structures. In certain cases, depending on the specific formula, when the voids are of molecular dimensions the compounds have been described as "molecular sieves" since only molecules that are less than a certain effective diameter are adsorbed within their structures. The experimental data presented in U.S. Pat. No. 4,477,418 show that a number of the listed hexacyanometallates exhibit $O_2$ versus $N_2$ adsorption selectivity. Selectivity is seen at short contact times but also, to a lesser extent, at apparent equilibrium conditions. Among the compositions studied there are wide variations in both the time-dependent (i.e. kinetic) and equilibrium values of the oxygen loading, $O_2/N_2$ selectivity (ratio of oxygen to nitrogen loading) and in the kinetics of oxygen adsorption. The data show an approximate inverse relationship between the rate of oxygen uptake and the $O_2/N_2$ selectivity which is consistent with a molecular sieving or size-selective physical adsorption process, one which is more favorable for entry of the smaller $O_2$ molecule.

A relatively limited number of solid state chemical $O_2$-selective sorbents are known. One of the oldest is the barium oxide/peroxide system disclosed by J. H. Hildebrand, *J. Amer. Chem. Soc.*, 34, 246 (1912), which on the basis of the reversible equilibrium: $BaO + \frac{1}{2} O_2 \rightleftarrows BaO_2$ at about 600° C. was once used in an industrial process for the separation of air. U.S. Pat. No. 3,980,763 discloses praseodymium oxide materials which bind $O_2$, converting it to an oxide ($O^{2-}$) ion. The process is temperature/pressure reversible at about 400° C.–500° C., advantage over $BaO_2$ of not being deactivated by atmospheric carbon dioxide. It is taught in U.S. Pat. No. 4,251,452 that solid manganese phosphine complexes reversibly absorb oxygen, however, the number of reversible oxygen adsorption and desorption cycles that can be obtained appears to be quite limited.

Solid state compositions prepared by an entrapment or encapsulation of a metal complex within the cage of a synthetic zeolite have been shown to function as reversible oxygen sorbents. R. S. Drago, et al., *J. Amer. Chem. Soc.*, 110. 304 (1988) and U.S. Pat. No. 4,830,999 both teach entrapment of the anionic cobalt(II) cyanide (cyanocobaltate(3−)) complexes as ionpaired species: $A^+{}_3[Co(CN)_5]^{3-}$ or possibly $A^+{}_2[Co(CN)_4]^{2-}$ ($A^+$ is $Na^+$, $Cs^+$, etc.) within the pores of a crystalline aluminosilicate zeolite, to yield solid state $O_2$-selective sorbents. While the compounds $A^+{}_3[Co(CN)_5]^{3-}$ dissolved in water or polar organic solvents are well known to bind oxygen (giving either superoxo or peroxo complexes, depending on conditions), the $O_2$-binding is always considered to be irreversible (Ref. G. A. Kozlov, et al., *i Teoreticheskava Eksperimental'nava Khimiva.* 17 (5) 686 (1984)). Thus for example, heating the superoxo complex, $[NEt_4]^+{}_3[O_2Co(CN)_5]'^-$, at 120° C. in vacuo gives only a mixture of decomposition products: $O_2$, $CO_2$, butene and other hydrocarbons. The observed reversible binding of $O_2$ by the same monomeric anionic complex in the zeolite, as described in U.S. Pat. No. 4,830,999, is attributed to as yet uncharacterized interactions between the complex and the walls of the zeolite cavity in which it resides. These interactions significantly change the nature (effectively alter the composition) of the complex such that it becomes reversibly $O_2$-binding.

While the entrapment of oxygen-carrier complexes in zeolites affords $O_2$-selective solid sorbents, there are significant disadvantages in this technique. Because of the need to incorporate (usually by ion-exchange methods) $Co^{2+}$ ions as well as the accompanying organic ligands (e.g. SALEN, $CN^-$, etc.) in zeolite cages of fixed and usually very small dimensions, and also at the same time retain a certain degree of "openness" within the structure for facile accessibility by $O_2$, the practical loading level of the active $O_2$-binding Co(II) species is often quite small. Thus, as taught by S. Imamura, et al., *Lanomuir.* 1, 326 (1985), in $[Co^{II}(BPY)(TERPY)]$-LiY, cobalt complex in LiY zeolite composition, the concentration of $Co^{II}$ active centers is only $1.05 \times 10^{-2}$ mmole/g of zeolite (giving a capacity of about 0.022 cc $O_2$/g). In the case of the $Co(CN)_5^{3-}/Co(CN)_4^{2-}$ in zeolite Y sorbent, although a relatively high concentration of $Co^{+2}$ (up to 7.1 wt % or 1.2 mmoles/g) can be incorporated, by spectroscopic measurements less than 1% of this cobalt is in an active $O_2$-binding configuration (Ref. R. J. Taylor, et al., *J. Amer. Chem. Soc.*, 111, 6610 (1989)). The second drawback of zeolite entrapped metal complex sorbents is their relatively high "background" adsorption capacity for $N_2$ which limits their $O_2/N_2$ selectivity in air separation applications. While the $Co(CN)_5^{3-}/Co(CN)_4^{2-}$ sorbent in zeolite Y at 40 torr pressure has a selectivity ($\alpha O_2/Ar$) of ~1.3 on the basis of data given in the above reference, the sorbent's oxygen to nitrogen selectivity, (because of the high natural adsorptivity of the latter), is calculated to be less than 1; i.e., about 0.7.

The objective in the art has been to develop easily synthesized solid state metal complex oxygen carriers which have a rapid reactivity and a high reversible equilibrium capacity for oxygen and a relatively low affinity for nitrogen. Additionally, such adsorbents should retain these properties in $O_2$ recovery applications over a long period of time. Prior to the present invention, no process has been taught which employs adsorbents which meet all of the above qualifications.

S. J. Carter, et al., *Inorg. Chem.* 25, 2888–2894 (1986) disclose the synthesis of what they believed to have been $Li_3[Co(CN)_5]\cdot 3DMF$, although they were unable to purify the material produced in their synthesis reaction. This reference teaches the use of this complex for cyanation reactions, and it is specifically stated that, based upon the research presented in the article, this compound would not be the preferred choice for such reactions. No mention is made of the suitability of this or any similar compound for reversibly binding oxygen. Carter also reported similar findings in a thesis entitled "Synthesis, Characterization and Reactions of New Organocyanocobaltates" Brandeis University, 1988. Additionally, Carter, et al., *J. Am. Chem. Soc.* 106, 4265–4266 (1984) report the isolation and characterization of $(PNP)_2Co(CN)_4$, although no mention is made for any uses of the complex.

SUMMARY OF THE INVENTION

The present invention is a class of solid state compositions comprising one or more cyanocobaltate complexes comprising a cobalt (II)-containing anion having from three and five cyanide ligands and having at least one cyanide stretching mode, as measured by infrared spectroscopy, in the range of 2074 $cm^{-1} \leq \nu_{CN} \leq 2140$ $cm^{-1}$. Additionally, the complex contains a charge-balancing cation having a molecular volume in excess of 40Å$^3$. The cation may be comprised of a solvated ion or may be a cationic complex, cluster or polymer. These solid state compositions are capable of selectively binding (i.e., sorbing) oxygen thereby making them useful for removing oxygen from oxygen-containing fluid streams. These complexes operate by chemically reacting with oxygen to form oxygenated stable complexes which are the corresponding oxygen adducts of the above cyanocobaltate complexes.

The above described process for selectively binding or sorbing oxygen can be reversed to cause the release of the bound oxygen to regenerate the complex and recover the oxygen. This can be achieved by heating the adduct or by any means which reduces the partial pressure of $O_2$ above the adduct, such as evacuating or passing a sweep gas over the adduct.

The above cyanocobaltate complexes are advantageous over prior art oxygen sorption materials in that the present solid state materials rapidly sorb oxygen, and even at equilibrum have a high capacity and selectivity for oxygen over nitrogen and other gases. This is due in part to the fact that these cyanocobaltate complexes have a reversible chemical affinity for oxygen, rather than relying primarily on their physical characteristics for adsorbing oxygen as is the case with zeolites and carbon molecular sieves. This chemical binding reduces or eliminates problems encountered in prior processes relating to kinetically dependent adsorption and poor adsorption at or near equilibrium conditions. An additional advantage in using the present complexes is that they can be used in a non-aluminosilicate environment (i.e., they do not have to be encapsulated in the cage of a zeolite) to reversibly bind oxygen.

DETAILED DESCRIPTION OF THE INVENTION

We have found that certain solid state compositions comprising cyanocobaltate complexes chemically react with oxygen to selectively sorb the gas and thus permit its separation and recovery from air or other fluid mixtures. The complexes are solid state materials wherein the active reversible $O_2$-binding species are anionic, pentacyano-, tetracyano- and lower cyanide coordination number complexes of cobalt. The process is operated by simply bringing an oxygen-containing fluid stream into contact with the solid state compositions, such as in typical temperature or pressure swing adsorption processes, although the present process can be used in any separation process designed for separating and/or scavenging oxygen, even in trace amounts, from a gas stream or from a liquid in which oxygen has been dissolved. Specific applications for this type of process include the separation of oxygen from gas streams containing oxygen and nitrogen, such as air, and for the separation of trace amounts of oxygen from a stream comprising predominently nitrogen or argon. Such a process is advantageous over prior art separation processes in that solid state complexes are used which reversibly bind oxygen, thereby allowing the sorbed oxygen to be recovered, and the sorbent (complex) to be regenerated by heating or by reducing the $O_2$ partial pressure over the adduct.

The oxygen-reactive sorbents used in the process are cyanometallates of cobalt(II) which contain at least three but not more than five cyanide ligands around the cobalt central metal atom ions, and which have at least one cyanide stretching mode, as measured by either infrared or Raman spectroscopy, in the range of 2074 $cm^{-1}$ to 2140 $cm^{-1}$. Additionally, all or part of the charge balancing is accomplished with a cation having a molecular volume in excess of 40Å$^3$ as defined by Mingos, D.M.P. et al. *Inorg Chem.* 20, 3769–71 (1991). We have found that materials falling outside of the specified ranges outlined above either fail to react with oxygen at an appreciable rate or they bind with $O_2$ so strongly that the absorbed oxygen cannot be removed from the adduct under reasonable conditions (i.e., conditions which would be feasible for the proposed uses or under conditions which do not cause decomposition of the sorbent itself). This cation may be comprised of a solvated ion or may be a cationic complex, cluster or polymer. The cyanocobaltate complexes which make up the solid state compositions can be represented by the general chemical formula:

$$[c]^{z+} [Co(CN)_n]^{x-} \cdot pS \; x/z$$

where
- c is a cation
- z is 1, 2 or 3;
- n is any number from 3 to 5;
- x is n−2;
- p is any number from 0 to 6; and
- S is a ligand which is capable of coordinating with $[c]^{z+}$, Co or both.

In several embodiments, c can be represented by the formula $[(A)_a(R_4N)_b]$.
where:
- A is alkali metal atom, alkaline earth metal atom, Zn, Cd or Hg atom;
- a is any number from 0 to 3;
- each R is independently $C_1$–$C_{10}$ substituted or unsubstituted alkyl, aryl or aralkyl; or a long chain hydrocarbon polymer;
- b is any number from 0 to 2.5, with the proviso that both a and b cannot be zero.

In the above structural formula, cyanide is ligated to cobalt through carbon while n, the number of cyanide ligands per cobalt atom ranges from a maximum of 5 to a minimum of 3. Since the formula represents an overall composition of a complex solid-state structure which may contain different $Co(CN)_n]^{x-}$ units (depending on the value of n), n in the above formula may be a fractional number. The cationic portion of the complex may contain an $R_4N$ cation, wherein each R is independently a $C_1$–$C_{10}$ substituted or unsubstituted alkyl, aryl or aralkyl group (although all four R groups cannot be aryl) or, alternatively, R can be a long chain hydrocarbon polymer such that $R_4N$, for example can be a nitrogen containing polymer such as Amberlyst. Instead of, or in addition to the $R_4N$, the cation portion of the complex may contain a cation, A, which is an alkali, alkali earth, Zn, Cd or Hg atom. The total cationic portion, $[(A)_a(R_4N)_b]^{z+}{}_{x/z}$, may also constitute two or three different cations with z separately ranging from 1 to 3, the number and total charge of the cations being so chosen as to maintain overall electrical neutrality for the structural formula. Typically z represents the charge of the cation alone, however, in cases where the ligand S has a charge and is associated with the cation, z represents the total charge of the cation along with the associated charged ligand.

The cobalt central metal ion in the above formula is in a divalent state, thus x=n−2. Since, however, there is the possibility that the overall composition expressed by the above formula contains $[Co(CN)_n]^{x-}$ units with different values of n, n and x in the formula may be fractional numbers.

In the formula, S represents a ligand, or several different ligands, either charged or neutral of total number p, wherein p may be any number from zero up to 6, including fractions since more than one structure represented by the above formula may be combined to form the total complex. These ligands (S) may coordinate to the $A^{z+}$ ion or to the cobalt ion (but only when n<5), or both. Unexpectedly, it has now been found that if the complex has a cationic molecular volume in excess of 40Å$^3$ and preferably in excess of 70Å$^3$, along with a cyanide stretching mode between 2074 cm$^{-1}$ and 2140 cm$^{-1}$ without the ligand S, then the presence of such a ligand is not necessary for the composition to reversibly bind oxygen. In some instances, however, it is the presence of this ligand, S, which results in the necessary cyanide stretching to allow for reversible oxygen sorption.

Representative examples of S when the ligand is bound to the $A^{z+}$ ion include: CN$^-$, N,N-dialkyl formamides (preferably DMF), N,N-dialkylamides and alkyl lactams (preferably N,N dimethylacetamide, N-methyl-2-pyrrolidinone and N-methyl piperidone), N-alkyl imides such as N-methyl succinimide, ammonia and potentially chelating tertiary amines such as N,N,N',N'-tetramethyl ethylenediamine and hexamethylenetetramine, as well as organic carbonates, acetone, sulfur-oxygen, and phosphorus-oxygen compounds.

Representative examples of S when the ligand is bound to the cobalt atom include: N-heterocycles such as pyridine, alkyl or perfluoroalkyl ring-substituted pyridines, N-methylimidazole and 1,2; 1,3 and 1,4-diazines: bipyridyls and alkyl or perfluoroalkyl ring-substituted dipyridyls; amines such as triethylenediamine and hexamethylenetetramine; pyrazine, organic nitriles such as dicyanogen, N≡C—C≡N, acetonitrile, benzonitrile, t-butylnitrile, and dicyanoalkanes: N≡C(CH$_2$)$_n$C≡N where n'=1 to 4; cyanamides such as the cyanamide or dicyanamide anion, N≡C—N—C≡N; the dicyanomethane (anion), N≡C—CH—C≡N; H$_2$O; alcohols, such as methanol; polymers containing polyvinyl pyridine or pyrrolidone; and halide and pseudohalide ions such as Cl$^-$, F$^-$, SCN$^-$, and NCS$^-$.

Where appropriate, the above ligands may be halogenated, in particular fluorinated, for greater stability towards oxidation, or additionally, may be polymeric analogues of any of the above. While it is required that there be some ligand (S) bound to the complex, additional molecules corresponding to any of the above compounds may be present as unbound solvate molecules.

These compositions are generally prepared by reacting a cobalt(II) halide or pseudohalide with an alkali metal or alkaline earth cyanide salt in a molar ratio of 1Co$^{2+}$:nCN$^-$, in a polar solvent (usually corresponding to the ligand (S) in the formula). Solids thus formed may be per se reactive towards O$_2$ or may be activated for reversible binding of O$_2$ by judicial heating or drawing a vacuum to expel a portion of the ligand S, or altering the ligands by solvent replacement. Compositions containing divalent or trivalent (z=2,3) ions may be prepared by the direct reaction of Co(II) halides with cyanide compounds of these ions or by metathetical reactions of solutions containing $[Co(CN)_n]^{x-}$ species with suitable sources of the cations.

In the present process, these compositions act as chemical sorbents for oxygen wherein the sorbed oxygen is attached to the cobalt(II) to form the oxygen adduct of the solid-state cyanometallate complex. Chemical bonding of oxygen with these complexes to form the oxygen adducts of the respective complexes is accompanied by changes in the UV/visible spectrum of the complex, the appearance of an O—O stretching frequency ($\nu_{O-O}$) which is significantly lower than that of free gaseous (or physically adsorbed) oxygen, and also by a "blue shift" in the $\nu_{CN}$ vibration. These analytical techniques were used to determine that, unlike the prior art hexacyanometallates, the compositions used in the present process chemically and reversibly bind oxygen. Without being bound by theory, it is believed that the ability of the complexes used in the present process to reversibly bind oxygen is made possible by reducing the electron density on cobalt through the use of countercations $[(A)_a(R_4N)_b]^{z+}$ having a molecular volume in excess of 40Å$^3$ which are able to interact with the nitrogen of the cyanide ligand to form $Co^{II}$—CN—A$^{z+}$—NC—$Co^{II}$ linkages. The importance of the bulky groups are to keep the metal centers apart and prevent the structure from collapsing. We have found that even small cations like Li$^+$ and Na$^+$, when used in combination with the appropriate solvent will generate sizes greater than 40Å$^3$. The effect is moderated by maintaining a cyanide stretching mode in the range of 2074 cm$^{-1}$ to 2140 cm$^{-1}$. The cyanide stretching frequency of the complexes gives an idea of the electron density on the cobalt, which is related to the strength of the interaction with oxygen. This stretching mode is maintained by the appropriate choice of cations along with the number of CN molecules, or by the use of coordinating ligands S which by binding to the cation can weaken the —CN—A$^{z+}$ interaction. For example, the complex $(Et_4N)_3Co(CN)_5$, having its cyanide stretch at 2066 cm$^{-1}$, binds $O_2$ strongly and irreversibly. Replacement of an $Et_4N$ group with Li$^+$ to give $(Et_4N)_2LiCo(CN)_5$ gives a major band at 2080 cm$^{-1}$ indicating loss of electron density from cobalt. The interaction of this complex with oxygen is reversible. The electron density can also be affected by the removal of one or more cyanide groups. As the cyanide frequency reaches 2140 cm$^{-1}$, as in the case of totally substituted zinc complexes, the interaction with oxygen becomes too weak to be of commercial value.

By thus controlling the electron density on cobalt not only is the binding of $O_2$ onto the $[Co^{II}(CN)_n]^{x-}$ unit rendered reversible, but its affinity for oxygen (i.e., the equilibrium binding constant for $O_2$) may be predictably altered.

The complexes of the present invention can be prepared by reaction of a cobalt(II) salt with a cyanide source in an appropriately chosen solvent. The resulting products can optionally be further reacted to exchange all or part of the cations or they can be reacted with other ancillary ligands. Suitable cobalt sources include (but are not limited to): cobalt dichloride ($CoCl_2$), cobalt dibromide ($CoBr_2$), cobalt diiodide ($CoI_2$), cobalt cyanide ($Co(CN)_2$), cobalt thiocyanate ($Co(SCN)_2$), cobaltous acetate ($Co(O_2CCH_3)_2$), cobaltous perchlorate ($Co(ClO_4)_2$), and cobaltous tetrafluoroborate ($Co(BF_4)_2$). Suitable cyanide sources would include (but are not limited to): sodium cyanide (NaCN), lithium cyanide (LiCN), potassium cyanide (KCN), cesium cyanide (CsCN), tetraethylammonium cyanide (($Et_4N$)CN), tetrabutylammonium cyanide (($Bu_4N$)CN), methyltributylammonium cyanide ((Me$Bu_3N$)CN), trimethylsilylcyanide ($Me_3SiCN$), and bis(triphenylphosphoranylidene)ammonium cyanide ($[Ph_3P)_2N]CN$).

The metal complex selective $O_2$-sorbent compositions are especially suitable for use in both pressure swing absorption (PSA) and temperature swing absorption (TSA) processes for the separation of air to recover oxygen or nitrogen or both.

In the pressure swing method, air (preferably dry) at ambient temperature and at pressures ranging from 1 to about 10 atm is passed through a column containing a fixed bed that is packed with the above cyanocobaltate solid absorbents. Oxygen is selectively absorbed by the packed bed resulting in an effluent of nearly pure nitrogen. The absorbent may take up as much as 2.3 mmoles of $O_2$ per gram. At the end of this absorption step the bed is rinsed and the resulting oxygenated solid in the bed is regenerated. In this type of cycle, since oxygen is being sorbed, it is preferable that the bed is rinsed with oxygen, such as by using a portion of the oxygen product produced by the cycle. This may be done by lowering the pressure of the atmosphere above the absorbent bed to about ambient conditions or by partially evacuating it to subambient pressures as low as 0.05 atm.

Alternatively, the desorption may be achieved by depressurizing the bed followed by purging it with some of the product nitrogen. The PSA methods described here may be used for the large scale production of oxygen or nitrogen from air, but are also useful for the removal of residual low levels of oxygen from nitrogen, argon and other gases that are inert to the cyanocobaltate absorbents.

In the temperature-swing method an oxygen-containing gas mixture, preferably a dry mixture, at from about 1 to 10 atm is passed through the absorbent column which results, as above, in a selective absorption of oxygen. In this case however, the regeneration of the absorbent is accomplished by heating. The desorption of $O_2$ may be assisted by also reducing the effective partial pressure of $O_2$ in the atmosphere above the absorbent by depressurization, partial evacuation to 0.1 to 0.3 atm, or by sweeping the bed with a pre-heated stream of some of the inert gas product. The latter is essentially a combined PSA/TSA process. Specific examples of PSA and TSA processes (though not with equilibrium $O_2$-selective sorbents) have been well described in the art.

In all of these processes the cyanocobaltate complexes are in the solid state and can be used in various forms such as powders, as single crystals, as pellets, as a slurry, or any other suitable form for the particular application.

The resultant oxygen adducts of the cyanometallate complexes which are formed during this process are unique structures which can be represented by the general chemical formula:

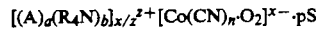

$$[(A)_a(R_4N)_b]_{x/z}{}^{z+}[Co(CN)_n\cdot O_2]^{x-}\cdot pS$$

where A, a, R, b, z, x, n, p and S are the same as set out above for the corresponding cyanocobaltate complexes. While the above chemical formula shows one oxygen molecule associated with the complex as written, there may, in some instances, be less than one oxygen molecule per this portion of the complex since the overall composition may contain more than one of the above structural units with a single oxygen molecule bound to several such units.

The following examples are presented to better illustrate the present invention and are not meant to be limiting.

EXPERIMENTAL

In the following Examples all chemical synthesis and oxygen sorbent handling operations were done (unless otherwise indicated) under cover of nitrogen or argon using standard Schlenk line, high vacuum line, or inert atmosphere dry box techniques. Reaction solvents were carefully dried and purified by distillation from $CaH_2$ (N,N-dimethylformamide, (DMF)), or from sodium benzophenone ketyl(diethyl-ether). Thermogravimetric (TGA) analysis experiments were carried out using Perkin Elmer TGS2 and DuPont 2950 instruments, which were equipped for performing measurements in either an $N_2$ or $O_2$ atmosphere. Infrared spectra were taken using a Nicolet 510 or a Perkin-Elmer 6000 series FTIR spectrometer; the reported vibrational frequencies are considered to be accurate to within $\pm 2$ cm$^{-1}$.

EXAMPLE 1:

Preparation of $(Et_4N)_{0.5}$ $Li_{2.5}$ $Co(CN)_5$ ·1.6 (acetone)

This complex was prepared via ion exchange between solid $(Et_4N)_3$ $Co(CN)_5$ and an excess of Lithium triflate dissolved in solution. The complex $(Et_4N)_3$ $Co(CN)_5$ (0.27 g. 0.465 mmole) was added as a solid to 50 ml of acetone containing (0.55 g, 3.5 mmole) Lithium triflate. The solution was stirred overnight. Even within an hour, the yellow $(Et_4N)_3$ $Co(CN)_5$ was observed to turn green because of ion exchange of the $Et_4N^+$ moeity with $Li^+$. After 18 hours the yellow green solid was filtered, washed with ether and dried. Yield=0.10 g. An infrared spectrum of this material showed that the cyanide bands were heavily split with bands at 2093, 2099, 2106, 2116 cm$^{-1}$. The coordinated acetone peaks at $\sim 1650$ cm$^{-1}$ were also heavily split. This may indicate a non uniform material due to differing amounts of acetone in various parts of the solid.

Elemental analysis: Calcd for $(Et_4N)_{0.5}$ $Li_{2.5}$ $Co(CN)_5$ 1.6 (acetone)

Calcd: C, 45.3; H, 5.06; N, 21.06; Li, 4.74; Co, 16.1
Found for the same batch:
C, 43.65; H 5.76; N, 21.84; Li, 4.51; Co, 15.4 C, 43.33; H 5.73; N, 20.77; Li, 4.51; Co, 15.4 Li : Co=2.5:1

Oxygen Reactivity of $(Et_4N)_{0.5}$ $Li_{2.5}$ $Co(CN)_5$ ·1.6 (acetone)

This solid complex was found to reversibly bind $O_2$, although the rate of $O_2$ uptake was relatively slow. A sample of this solid was loaded on a Perkin Elmer T. G. A. and $O_2$ was introduced. A 1.75% uptake was observed in 37 minutes. This desorbed 1.74% in 560 minutes, and showed similar uptake on resorption of $O_2$ (1.93% in 45 minutes).

EXAMPLE 2

Preparation of $(Et_4N)_{0.57}$ $Na_{2.43}$ $Co(CN)_5$ ·2.25 DMAC

A solution of $NaPF_6$ (0.33 g) in 50 ml DMAC was prepared. To this the complex $(Et_4N)_3$ $Co(CN)_5$ (0.15 g) was added as a solid, and the solution was stirred overnight. An aquagreen precipitate was filtered washed with DMAC (10 ml) and ether (20 ml). The infrared spectrum of this solid showed cyanide bands at 2107 cm$^{-1}$ (s), 2125 and a strong peak at 1614 cm$^{-1}$ due to DMAC. A peak at 784 cm$^{-1}$ seemed to indicate residual $Et_4N^+$. An elemental analysis of this complex gave Na, 10.48%, Co, 11.4%, which is a Na: Co ratio of 2.43 : 1. This was fitted to the formula shown above and the amount of DMAC attached to the sample was confirmed by heating to 160° C. and measuring the weight loss.

Oxygen reactivity of the complex

This complex was loaded on a Perkin Elmer T. G. A. and cycled with 5 min $O_2$/30 min $N_2$

| Cycle No | % Uptake |
| --- | --- |
| 1 | 0.59 |
| 2 | 0.39 |
| 3 | 0.27 |

The above results show that this complex reversibly sorbed oxygen, although the reversibility was rather poor, possibly due to rapid loss of solvent.

EXAMPLE 3

Preparation of $(Et_4N)_{1.5}Mg_{0.75}Co(CN)_5$ 0.5 DMF

The complex $(Et_4N)_3$ $Co(CN)_5$ (0.27 g.) was dissolved in 30 ml of acetonitrile. To this was added 15 ml of DMF in which was dissolved 0.075 g of Magnesium triflate. A green solution was obtained. Addition of 50 ml ether gave a cloudy solution. A yellow green precipitate was filtered and this was washed with ether followed by acetone and then ether again. Yield=0.13 g. An infrared spectrum of this sample showed a strong cyanide band at 2105 cm$^{-1}$, and a peak at 784 cm$^{-1}$ indicated the presence of the $Et_4N^+$ moiety, and a peak at $\sim 1650$ cm$^{-1}$ for DMF. A metals analysis for a bulk sample gave 13.2% Co, 4.13% Mg which is a Mg : Co ratio of 0.75 to 1. The C, H, N analysis of batches of this material were observed to fluctuate even within the same sample indicating possibly non uniform distribution of solvent. However, one batch gave an acceptable C, H, N analysis.

Calcd for $(Et_4N)_{1.5}Mg_{0.75}Co(CN)_5$ ·0.5 DMF Calcd: C, 50.60: N, 22.34; H, 7.63: Co,13.42; Mg, 4.15 Found: C, 51.06: N, 21.46; H, 7.55; Co, 13.2; Mg, 4.13

Oxygen reactivity of the Magnesium complex

A sample was loaded on a Perkin-Elmer T. G. A. and cycled with $O_2/N_2$ 5 min, 10 min, respectively.

| Cycle No | % Uptake |
| --- | --- |
| 1 | 1.11 |
| 13 | 0.83 |
| 25 | 0.61 |
| 39 | 0.54 |
| 60 | 0.48 |

Both sets of cycle data indicate that the complex of this example reversibly bound oxygen.

EXAMPLE 4

Synthesis of $(Bu_4N)_2Co(CN)_4$ ·$C_5H_5N$ $(Bu_4N)_2Co(CN)_4$ (0.242 g, 0.373 mmol) was dissolved in anhydrous pyridine (3 mL): a light green solution resulted. After five minutes at room temperature, anhydrous hexane (10 mL) was added to precipitate a greenish-yellow solid. The solid was filtered and washed thoroughly with hexane (3×10 mL) before it was suction filtered dry for $\sim 0.5$ hr. A light yellowish-green powder (0.235 g, 86% yield) which analyzed for $(Bu_4N)_2Co(CN)_4$ ·$C_5H_5N$ was obtained.

FTIR (Nujol): 2099 (w), 2079 (s), 2054 (sh), 2040 (w) cm$^{-1}$ (CN); 1589 (m) cm$^{-1}$ (pyridine). 2124 (w), 2098 (w), 2093 (w), 2078 (s), 2055 (sh), 2041 (w) cm$^{-1}$ (CN, after exposure to air).

Elemental Analysis (Found): Co, 7.72; C, 67.62; H, 10.51; N, 13.79. Expected for $(Bu_4N)_2Co(CN)_4$ ·$C_5H_5N$: Co, 8.10; C, 67.73; H, 10.68: N, 13.48.

A second batch of $(Bu_4N)_2Co(CN)_4 \cdot C_5H_5N$ (1.261 g, 92% yield) was prepared by the same procedure but at five times the scale.

TGA Studies of the Reversible Oxygen Binding Behavior of $(Bu_4N)_2Co(CN)_4 \cdot C_5H_5N$ A sample of $(Bu_4N)_2Co(CN)_4 \cdot C_5H_5N$ was loaded on a Perkin-Elmer TGA (under nitrogen). No weight loss occurred at 30° C. under nitrogen (30 min). On switching to oxygen (10 min), a weight gain of 3.25% was observed. Under nitrogen, a weight loss of 3.38% was seen after 30 min, and a second oxygenation resulted in a 3.84% weight gain. Subsequently, a total of 25 cycles were performed with excellent reversible oxygen binding (see Table 1). Interestingly, the color of the material changed from green to red on exposure to oxygen and changed back to green under nitrogen after ~15-20 minutes.

TABLE 1

Reversible Oxygen Binding Behavior of $(Bu_4N)_2Co(CN)_4 \cdot C_5H_5N$
(Cycle = Oxygen 10 min/Nitrogen 30 min)

| Cycle Number | Wt. Gain Under $O_2$ | Wt. Loss Under $N_2$ |
|---|---|---|
| 1 | 3.25% | 3.38% |
| 2 | 3.84% | 3.91% |
| 3 | 3.97% | 4.00% |
| 4 | 3.99% | 4.04% |
| 8 | 3.91% | 3.94% |
| 12 | 3.79% | 3.80% |
| 15 | 3.67% | 3.71% |
| 20 | 3.55% | 3.58% |
| 24 | 3.44% | 3.50% |
| 25 | 3.42% | — |

A fresh sample of $(Bu_4N)_2Co(CN)_4 \cdot C_5H_5N$ was oxygenated for 60 minutes and a weight gain of 3.97% (90% of the calculated stoichiometric uptake for $(Bu_4N)_2Co(CN)_4 \cdot C_5H_5N$) was seen after ~30 minutes. Desorption under nitrogen for 90 minutes resulted in a 4.14% weight loss. Subsequent cycling looked similar to that shown above.

EXAMPLE 5

Synthesis of $[(Bu_4N)_2Co(CN)_4] \cdot C_4H_6N_2$ $(Bu_4N)_2Co(CN)_4$ (0.313 g, 0.483 mmol) was dissolved in anhydrous 1-methylimidazole (5 mL); a greenish-yellow solution resulted. After five minutes at room temperature, anhydrous THF (20 mL) and anhydrous hexane (20 mL) were added to crash out a green oil. On vigorously stirring the mixture for ~10 minutes, a fluffy light green powder resulted. The powder was filtered and washed thoroughly with hexane (10 mL) and diethyl ether (2×10 mL) before it was suction filtered dry for ~3.5 hr. A light green powder (0.281 g, 80% yield) which analyzed for $[(Bu_4N)_2Co(CN)_4] \cdot C_4H_6N_2$ was obtained.

FTIR (Nujol): 2170 (vw), 2100 (w), 2088 (sh), 2078 (s), 2053 (sh), 2039 (w) cm$^{-1}$ (CN).

2110 (w), 2089 (sh), 2078 (s), 2053 (sh), 2039 (w) cm$^{-1}$ (CN, after exposure to air).

Elemental Analysis (Found): Co, 7.81; C, 66.14; H, 10.39; N, 15.56. Expected for: Co, 8.07: C, 65.81: H, 10.77; N, 15.35. $[(Bu_4N)_2Co(CN)_4] \cdot C_4H_6N_2$

TGA Studies of the Reversible Oxygen Binding Behavior of $[(Bu_4N)_2Co(CN)_4] \cdot C_4H_6N_2$ A sample of $[(Bu_4N)_2Co(CN)_4] \cdot C_4H_6N_2$ was loaded on a Perkin-Elmer TGA (under nitrogen). No weight loss occurred at 30° C. under nitrogen (30 min). On switching to oxygen (10 min), a weight gain of 3.15% was observed. Under nitrogen, a weight loss of 0.36% was seen after 30 min, and a second oxygenation resulted in a 0.67% weight gain. Subsequently, a total of 12 cycles were performed with reversible oxygen binding (see Table 2). This material uptakes oxygen much faster than it desorbs oxygen at 30° C.

TABLE 2

Reversible Oxygen Binding Behavior of $[(Bu_4N)_2Co(CN)_4] \cdot C_4H_6N_2$
(Cycle = Oxygen 10 min/Nitrogen 30 min)

| Cycle Number | Wt. Gain Under $O_2$ | Wt. Loss Under $N_2$ |
|---|---|---|
| 1 | 3.15% | 0.36% |
| 2 | 0.67% | 0.23% |
| 3 | 0.28% | 0.18% |
| 8 | 0.17% | 0.17% |
| 11 | 0.18% | 0.16% |
| 12 | 0.14% | — |

If this material is heated to 100° C. for 60 minutes (under nitrogen) and temperature swing cycling is done ($O_2$: 10 min at 30° C./$N_2$: 5 min at 30° C., 5° C./min to 70° C., 70° C. for 30 min, 10° C./min to 30° C., 30° C. for 20 min), completely reversible cycles can be attained.

EXAMPLE 6

Synthesis of $(Et_4N)_{1.9}Li_{1.1}(CoCN)_5$

A solution of lithium triflate (1 g, 6.4 mmole) in 100 ml of DMAC was prepared. To this was added (0.45 g, 0.77 mmole) of $(Et_4N)_5'$ as a solid and this was stirred overnight, ~16 hours. The green solid was filtered and washed with acetone (20 ml) followed by ether and dried. Yield=0.28 g. The infrared spectrum of this solid showed cyanide bands at 2080, 2986, 2096, 2113 (cm$^{-1}$) and a very low intensity band due to residual solvent at ~1614 cm$^{-1}$. Upon heating to 80° C. for several hours under $N_2$ this band was observed to disappear. A sample given for elemental analysis was observed to fit to $(Et_4N)_{1.9}Li_{1.1}Co(CN)_5$.

Calcd: C,54.65; H,8.56; N,21.77; Li1.72; Co,13.27
Found: C,54.17; H,8.22; N,20.4; Li1.61; Co,12.9 Found for a second batch: Li1.72; Co,13.1

Oxygen reactivity of $(Et_4N)_{1.9}Li_{1.1}Co(CN)_5$

A sample was loaded on a Perkin Elmer T.G.A. and $O_2$ was introduced and the sample was found to pick up 3.8% by weight in 60 min. The sample was desorbed for 50 min. under $N_2$ and then cycled with $O_2$ (10 min), $N_2$ (50 min).

| Cycle No. | % Uptake |
|---|---|
| 1 | 2.27 |
| 5 | 2.43 |
| 8 | 2.39 |
| 26 | 2.14 |
| 32 | 2.08 |
| 40 | 2.14 |

The overall uptake of $O_2$ in a given time seemed to depend on the batch of starting material $(Et_4N)_3Co(CN)_5$ used to prepare the compound. For example another batch of material observed 4.6% in 60 minutes. This could have to do with the surface area of the starting material since this is a solid state reaction.

EXAMPLE 7

Synthesis of $(Et_4N)_2 Zn_{0.5}Co(CN)_5$

The complex $(Et_4N)_3Co(CN)_5$ (0.25 g) was dissolved in 40 ml DMF and stirred to get a green solution. To this was added a solution of 0.078 g of Zinc triflate in 35 ml DMF. The addition was done over a period of 5 min. The color of the solution turned dark green and the addition of ether precipitated a green solid which was filtered, washed with ether and dried in vacuo. Yield=0.20 g. The infrared spectrum of this sample showed cyanide bands at 2098, 2117 cm$^{-1}$. Very little to no DMF was observed in the spectrum. A metals analysis of the sample gave Co 11.8%, Zn 6.44%, a Zn to Co ratio of 0.5 to 1.

Calcd: C,52.32: H,8.30; N,20.34; Co,12.23; Zn,6.78
Found: {C,49.4: H,8.50: N,20.36}Co,11.8; Zn,6.44 {C,55.71: H,8.01: N,19.80}

The carbon analysis was found to fluctuate dramatically in the same sample indicating non-uniformity of the sample. For this reason the preparation was repeated and the metals analysis was found to be reproducible. Found Co, 12.0%, Zn 6.7%.

Oxygen Reactivity

The complex was found to bind $O_2$ reversibly. The results of a cycling experiment 5 min $O_2$/20 min $N_2$ are shown below:

| Cycle No. | Wt % |
| --- | --- |
| 1 | 2.77 |
| 2 | 1.68 |
| 3 | 1.24 |
| 20 | 0.91 |
| 116 | 0.60 |

EXAMPLE 8

Synthesis of $(Bu_4N)_2Co(CN)_4$ $(Bu_4N)CN$ (8.437 g, 31.42 mmol) was dissolved in anhydrous THF (95 mL). This clear, colorless solution was filtered (using 55 mL THF to rinse) and then added to a filtered solution of $CoCl_2$ (1.020 g, 7.856 mmol) in THF (395 mL) at room temperature. Additional THF (5 mL) was used to ensure complete transfer. Upon addition, the reaction became emerald green and clear, but, over ~5-10 minutes's time, white precipitate began to come out of solution. The reaction was stirred at room temperature for 10 min before it was filtered to leave a white crystalline solid in the frit. This white material (with a faint greenish tint) was washed with dry THF (3×20 mL) and dry hexane (3×20 mL) and suction filtered dry for ~1 hr to yield 3.510 g (5.42 mmol, 69% yield) of white powder which analyzed for $(Bu_4N)_2Co(CN)_4$.

Analytical Data for $(Bu_4N)_2Co(CN)_4$: FTIR (Nujol): 2114 (sh), 2095 (s), 2072 (sh), 2056 (w) cm$^{-1}$ (CN). 2163 (w), 2124 (sh), 2105 (s) cm$^{-1}$ (after exposure to air)

Elemental Analysis (Found): Co, 9.14: C, 66.65; H, 10.88; N, 12.70. Expected for $(Bu_4N)_2Co(CN)_4$: Co, 9.10; C, 66.73; H, 11.20; N, 12.97.

TGA Studies of the Reversible Oxygen Binding Behavior of $(Bu_4N)_2Co(CN)_4$ A sample of $(Bu_4N)_2Co(CN)_4$ was loaded on a Perkin-Elmer TGA (under nitrogen). No weight loss occurred at 30° C. under nitrogen (30 min). On switching to oxygen (10 min), a weight gain of 2.65% was observed. Under nitrogen, a weight loss of 1.51% was seen after 30 min, and a second oxygenation resulted in a 1.53% weight gain. Interestingly, the color of the material had changed to a khaki green after 1 cycle. Subsequently, 15 more cycles were performed with reasonably good reversible oxygen binding (see Table 3). After this room temperature cycling, the sample was heated to 70° C. for 30 min; a 0.87% weight loss was seen. Another $O_2/N_2$ cycle at 30° C. resulted in a weight gain of 0.29% under oxygen and a weight loss of 0.25% under nitrogen.

TABLE 3

Reversible Oxygen Binding Behavior of $(Bu_4N)_2Co(CN)_4$
(Cycle = Oxygen 10 min/Nitrogen 30 min)

| Cycle Number | Wt Gain Under $O_2$ | Wt. Loss Under $N_2$ |
| --- | --- | --- |
| 1 | 2.65% | 1.51% |
| 2 | 1.53% | 0.89% |
| 3 | 0.86% | 0.59% |
| 4 | 0.61% | 0.54% |
| 10 | 0.44% | 0.41% |
| 16 | 0.36% | 0.34% |
| 17 | 0.35% | — |
|  | heated to 70° C. |  |
| 18 | 0.29% | 0.25% |

In a separate experiment, a sample of $(Bu_4N)_2Co(CN)_4$ was loaded on a DuPont TGA (under nitrogen). This time the sample was exposed to oxygen until no further weight gain could be detected; this point was reached after ~60 min, but the sample was left under oxygen for 80 min. A 4.49% weight gain was observed (essentially 1 eq of $O_2$ per eq of Co). The sample was then purged with nitrogen for 240 min and a 2.50% weight loss was seen (a plateau had just about been reached). Subsequent cycles consisted of 30 min under oxygen and 90 min under nitrogen (see Table 4).

TABLE 4

Reversible Oxygen Binding Behavior of $(Bu_4N)_2Co(CN)_4$
(Cycle = Oxygen 30 min/Nitrogen 90 min)

| Cycle Number | Wt Gain Under $O_2$ | Wt. Loss Under $N_2$ |
| --- | --- | --- |
| 1 | 4.49%* | 2.50%* |
| 2 | 0.77% | 0.65% |
| 3 | 0.55% | 0.54% |
| 4 | 0.47% | 0.47% |
| 7 | 0.36% | 0.36% |
| 9 | 0.32% | 0.32% |
| 11 | 0.28% | 0.28% |

*80 min under oxygen/240 min under nitrogen

EXAMPLE 9

Synthesis of $(Cp_2Co)_2Co(CN)_4 \cdot 0.62DMF$ $Cp_2CoPF_6$ (1.134 g, 3.394 mmol, 6.0 eq) was dissolved in anhydrous DMF (20 mL) and then filtered. Additional DMF (10 mL) was used to try to dissolve the dark brown residue which remained in the frit, but the material remained insoluble. The combined orange filtrates were transfered to a beaker, and additional DMF (5 mL) was used to ensure complete transfer. $(Bu_4N)_2Co(CN)_4$ (0.367 g, 0.566 mmol) was dissolved in DMF (20 mL). This blue solution was added, with stirring, to the $Cp_2CoPF_6$ solution over approximately one minute's time. Immediately, the solution became green and opaque. The mixture was stirred at room temperature for 30 minutes before it was filtered, but the fine particles went through the frit.

Diethyl ether (20 mL) was added to form a flocculent precipitate which filtered down to a green goo in the frit. Washing the goo with DMF (10 mL) caused the precipitate to go through the frit again, so more ether (10 mL) was added to re-coagulate the material. The goo was washed with ether (3×10 mL) and suction filtered dry for ~1.5 hr. A dark green powder (0.127 g) was obtained.

FTIR (Nujol): 2150 (sh), 2116 (m), 2088 (s) cm$^{-1}$ (CN); 1662 (m) cm$^{-1}$ (DMF). 2150 (sh), 2123 (s), 2099 (sh) cm$^{-1}$ (CN); 1128 (m) cm$^{-1}$ (Co-O$_2^-$) after exposure to air.

Elemental Analysis (Found): Co, 30.1; C, 49.26; H, 3.56; N, 11.42. Expected for (Cp$_2$Co)$_2$-Co(CN)$_4$·0.62DMF: Co, 30.1: C, 52.95: H, 4.18: N, 11.03.

A sample of the material was loaded on the Perkin-Elmer TGA under nitrogen. Initially, the sample lost a little bit of weight while under nitrogen (0.18% in 30 min). On switching to oxygen for 10 minutes, a 1.47% weight gain was seen, and a 1.08% weight loss was seen over 30 minutes under nitrogen. A total of 17 cycles were performed with reasonably good reversibility (Table 5).

TABLE 5

Reversible Oxygen-Binding Behavior of (Cp$_2$Co)$_2$Co(CN)$_4$·0.6DMF
(Cycle = Oxygen 10 min/Nitrogen 30 min)

| Cycle Number | Wt. Gain Under O$_2$ | Wt. Loss Under N$_2$ |
|---|---|---|
| 1 | 1.47% | 1.08% |
| 2 | 0.84% | 0.75% |
| 5 | 0.62% | 0.64% |
| 10 | 0.50% | 0.48% |
| 15 | 0.35% | 0.34% |
| 17 | 0.32% | 0.32% |

EXAMPLE 10

Synthesis of Na$_{2.2}$Co(CN)$_{4.2}$·2.1NMP·1.6NaCl

Solid NaCN (0.294 g, 6.00 mmol, 4.00 eq) was ground as finely as possible, and it was dissolved in NMP (100 mL) by stirring the mixture at room temperature for 16 hr and with heating for 0.5 hr. The NaCN solution was filtered to remove a few specks of undissolved material, and the filtrate was added over two minutes's time to a solution of CoCl$_2$ (0.195 g, 1.50 mmol) in NMP (15 mL). An emerald green solution resulted (Co(II) concentration = 1.3×10$^{-2}$M). After 15-20 minutes of stirring at room temperature, a very fine precipitate was visible on the sides of the flask, but after a total of 2.5 hr at room temperature, a filtration was unsuccessful. Therefore, diethyl ether (110 mL) was added to the mixture and stirring was continued for another hour. The mixture was filtered to leave a green goo in the frit. The goo was washed with diethyl ether (3×20 mL), and a blue powder (0.563 g) resulted. The powder was dried under vacuum (~10$^{-3}$ mmHg, room temperature, 20 hr) to yield 0.548 g of blue-green product.

FTIR (Nujol): 2114 (sh), 2089 (s), 2019 (vw,sh), 1982 (w) cm$^{-1}$ (CN) 1661 (vs) cm$^{-1}$ (NMP)

Elemental Analysis (Found): Na, 16.6; Co,11.2; Cl, 11 (1.6 eq NaCl) Na/Co ratio=2.2 (NaCl subtracted)

Best approximation of the composition of this material is: "Na$_{2.2}$Co(CN)$_{4.2}$·2.1NMP·1.6NaCl"

A sample of this material was loaded on the DuPont TGA (under nitrogen). Reasonably good reversible oxygen binding occurred without heat treatment, and very little solvent loss occurred at 30° C. The results of this cycling are shown in Table 6. Heating this sample to 80° C. for 30 minutes reduced its oxygen sorbing activity.

TABLE 6

Oxygen/Nitrogen Cycling Data for "Na$_{2.2}$Co(CN)$_{4.2}$·2.1NMP·1.6NaCl":

| Cycle Number | % Wt. Gain (O$_2$) | % Wt. Loss (N$_2$) |
|---|---|---|
| 1 | 1.55 | 0.73 (60 min)* |
| 2 | 0.53 | 0.44 |
| 3 | 0.35 | 0.42 (45 min)* |
| 4 | 0.31 | 0.31 |
| 5 | 0.24 | 0.29 |
| 6 | 0.22 | 0.26 |
| 7 | 0.19 | 0.24 |
| 8 | 0.17 | — |

*Other desorptions were done for 30 min under nitrogen

EXAMPLE 11

Synthesis of Na$_{1.8}$Co(CN)$_{3.8}$·2.0DMF·1.3NaCl

To a solution of NaCN (0.731 g, 14.9 mmol, 4.00 eq) in DMF (~200 mL) was added a solution of CoCl$_2$ (0.484 g, 3.73 mmol) in DMF (20 mL). Additional DMF (5 mL) was used to ensure complete transfer. An emerald green solution resulted (Co(II) concentration = 1.6×10$^{-2}$M). After 1.5 hours of stirring at room temperature, the mixture was more of a dark blue color and very fine precipitate was visible on the sides of the flask. Diethyl ether (75 mL) was added to the mixture and stirring was continued for 3.5 hours. The mixture was filtered to leave a dark green-blue goo in the frit and a dark green filtrate. The goo was washed with DMF (2×30 mL) and then with diethyl ether (3×20 mL); the royal blue powder (0.530 g) was dried under vacuum (~10$^{-3}$ mmHg, room temperature, 20 hr).

FTIR (Nujol): 2101 (sh), 2092 (s), 2021 (w), 1996 (vw), 1983 (w) cm$^{-1}$ (CN) 1658 (vs), 1603 (sh) cm$^{-1}$ (DMF)

Elemental Analysis (Found): Na, 17.0; Co, 13.9; Cl, 11 (1.3 eq NaCl) Na/Co ratio=1.8 (NaCl subtracted)MW 424

Best approximation of the composition of this material is: "Na$_{1.8}$Co(CN)$_{3.8}$·2.0DMF·1.3NaCl"

A sample of this material was loaded on the DuPont TGA (under nitrogen). Reasonably good reversible oxygen binding occurred without heat treatment; however, some solvent loss occurred at 30° C. The results of this cycling are shown in Table 7. Heating this sample to 100° C. for ~25 minutes virtually eliminated its oxygen sorbing activity.

TABLE 7

Oxygen/Nitrogen Cycling Data for "Na$_{1.8}$Co(CN)$_{3.8}$·2.0DMF·1.3NaCl":

| Cycle Number | % Wt. Gain (O$_2$) | % Wt. Loss (N$_2$) |
|---|---|---|
| 1 | 1.95 | 1.07 (60 min)* |
| 2 | 0.36 | 0.48 |
| 3 | 0.22 | 0.39 |
| 4 | 0.16 | 0.33 |
| 5 | 0.14 | 0.28 |
| 6 | 0.12 | 0.25 |
| 7 | 0.10 | 0.22 |
| 8 | 0.09 | — |

*Other desorptions were done for 30 min under nitrogen

EXAMPLE 12 (COMPARATIVE)

Synthesis of "Cs$_2$Co(CN)$_4$·0.84 DMF"

Cesium triflate was prepared by mixing methanolic solutions of cesium chloride (3.1 mmol) and silver triflate (2.6 mmol). The silver chloride that precipitated was filtered off through Celite and the filtrate was evaporated to dryness. The cesium triflate (with unreacted cesium chloride still present) was taken up in DMF (125 ml) and filtered to yield a solution of clean cesium triflate which was used in the subsequent reaction.

(Bu$_4$N)$_2$Co(CN)$_4$ (0.440 g, 0.679 mmol) was dissolved in anhydrous DMF (10 mL). This solution was added to the filtered solution of cesium triflate in DMF (125 mL). Additional DMF (5 mL) was used to ensure complete transfer. The color of the cobalt mixture became a pale brownish-yellow and very fine precipitate came out of solution. The mixture was unsuccessfully filtered, and then 50 mL of diethyl ether were added in order to coagulate the product. Filtration then yielded a dark brown sludge which was washed with DMF (10 mL), diethyl ether (20 mL), and hexane (2×10 mL) to yield a brown powder. The sample was suction filtered dry for ~1 hour to yield 0.268 g of material.

FTIR (Nujol): 2105 (s), 2086 (s), 2046 (sh) cm$^{-1}$ (CN); 1659 (s) cm$^{-1}$ (DMF) 2183 (sh), 2122 (sh), 2105 (s), 2086 (s) cm$^{-1}$ (CN, after exposure to air); no Co(III) superoxo stretch was seen Elemental Analysis (Found): Co, 12.0; Cs, 54.8 Cs/Co ratio=2.02 Calcd for Cs$_2$Co(CN)$_4$·0.84 DMF: Co, 12.02; Cs, 54.22

TGA Studies of the Oxygen Binding Behavior of "Cs$_2$Co(CN)$_4$·0. 84 DMF"

A sample of "Cs$_2$Co(CN)$_4$·0.84 DMF" was loaded on a Perkin-Elmer TGA (under nitrogen). Weight loss occurred at 30° C under nitrogen (0.36% in 30 min). On switching to oxygen for 20 minutes, a weight gain of 1.04% was seen. Unfortunately, desorption under nitrogen was extremely small (0.09% in 30 minutes). Therefore, the sample was heated to 80° C. for 30 minutes; only a 1.23% weight loss was seen. Oxygenation at 30° C. for 20 minutes resulted in a 0.18% weight gain but only a 0.05% weight loss was seen when the sample was purged with nitrogen while heating to 50° C. for 30 minutes. Finally, the sample was heated to 160° C. for 30 minutes and a weight loss of 2.04% was seen before a plateau and no further weight loss was seen. Oxygenation at 30° C. then resulted in a 0.24% weight gain, but no weight loss was seen under nitrogen on heating to 120° C. for ~15 minutes. This material appears to be an irreversible oxygen binder.

EXAMPLES 13-22

Various other complexes were synthesized and tested for reversible O$_2$ binding in accordance with the general procedures set out above. The complex structures, cation volume, infrared stretching bands and results of O$_2$ testing are set out in Table 8 below. For ease of reference, the data for the complexes synthesized in Examples 1-12 are also set out in Table 8.

TABLE 8

| Example | Complex | Cation Volume (Å) | Infrared (cm$^{-1}$) | Reversible O$_2$ Binding |
|---|---|---|---|---|
| 1 | (Et$_4$N)$_{0.5}$Li$_{2.5}$[Co(CN)$_5$]·1.6 acetone | 80.25$^c$ | 2093, 2099, 2106, 2116 | Yes |
| 2 | (Et$_4$N)$_{0.57}$Na$_{2.43}$Co(CN)$_5$]·2.25 DMAc | 126.75$^c$ | 2107, 2125 | Yes |
| 3 | (Et$_4$N)$_{1.5}$Mg$_{0.75}$[Co(CN)$_5$]·0.5 DMF | 135.75$^c$ | 2105 | Yes |
| 4 | (Bu$_4$N)$_2$[Co(CN)$_4$]·pyridine | 265.00$^h$ | 2079(s) | Yes |
| 5 | (Bu$_4$N)$_2$[Co(CN)$_4$]·1-Me-imidazole | 265.00$^h$ | 2078(s) | Yes |
| 6 | (Et$_4$N)$_{1.9}$Li$_{1.1}$[Co(CN)$_5$] | 135.75$^c$ | 2080, 2086, 2096, 2113 | Yes |
| 7 | (Et$_4$N)$_2$Zn$_{0.5}$[Co(CN)$_5$] | 135.75$^c$ | 2117, 2098 | Yes |
| 8 | (Bu$_4$N)$_2$[Co(CN)$_4$] | 265.00$^h$ | 2095(s) | Yes |
| 9 | (Cp$_2$Co)$_2$[Co(CN)$_4$]·0.6 DMF | 127.88$^j$ | 2115(m), 2088(s) | Yes |
| 10 | Na$_{2.2}$[Co(CN)$_{4.2}$]·2.1 NMP·1.6 NaCl | 134.25$^f$ | 2114(sh), 2089(s) | Yes |
| 11 | Na$_{1.8}$[Co(CN)$_{3.8}$·2.0 DMF·1.3 NaCl | 114.75$^g$ | 2101(sh), 2092(s) | Yes |
| 12 | Cs$_2$[Co(CN)$_4$]·0.8 DMF | 18.38$^i$ | 2105(s), 2086(s) | No |
| 13 | Mg$_{1.5}$[Co(CN)$_5$]·2 DMF | 89.12$^b$ | 2122(s), 2156 | Yes |
| 14 | Li[Co(CN)$_3$]·2 DMF | 90.12$^d$ | 2115 | Yes |
| 15 | (Et$_4$N)$_{0.5}$(Ph$_3$Sn)$_{2.5}$[Co(CN)$_5$] | 241.00$^{c,e}$ | 2114 | Yes |
| 16 | Li$_3$[Co(CN)$_5$]·2 DMF | 90.12$^d$ | 2087, 2101, 2117 | Yes |
| 17 | Li$_3$[Co(CN)$_5$]·3 DMAc | 105.38$^k$ | 2100 | Yes |
| 18 | Zn$_{1.5}$[Co(CN)$_5$· X 0.5 DMF | 78.12$^a$ | 2140(s) | Very Weak |
| 19 | Cs$_3$[Co(CN)$_5$]·1.5 DMF | 18.38$^i$ | 2078 | No |
| 20 | (Cp$_2$Co)$_3$[Co(CN)$_5$]·DMF | 177.88$^j$ | 2070 | No |
| 21 | (Et$_4$N)$_3$[Co(CN)$_5$] (ref.1) | 135.75$^c$ | 2066 | No |
| 22 | (Bu$_4$N)$_3$[Co(CN)$_5$] (ref.1) | 265.00$^c$ | 2066 | No |

$^a$(Zn.DMF)$^{+2}$; $^b$(Mg.DMF)$^{+2}$; $^c$(Et$_4$N)$^+$; $^d$(Li.DMF)$^+$; $^e$(Ph$_3$Sn)$^+$; $^f$(Na.NMP)$^+$; $^g$(Na.DMF)$^+$; $^h$(Bu$_4$N)$^+$; $^i$DMF not associated with Cs, see text; $^j$(Cp$_2$Co)$^+$; $^k$(Li.DMAc)$^+$; $^l$White, Solodar, Baizer Inorganic Chemistry Abbreviations:
DMF = N,N-dimethylformamide, DMAc = N,N-dimethylacetamide, NMP = N-methylpyrrolidinone, Cp = η$^5$-cyclopentadienyl From the results presented above, it can be seen that complexes having a cyanide stretch between 2074 cm$^{-1}$ and 2140 cm$^{-1}$ along with a cation volume of greater than 40Å$^3$, reversibly bind oxygen, whereas those complexes falling outside of these ranges do not reversibly bind oxygen.

Having thus described the present invention, what is now deemed appropriate for Letters Patent is set out in the following appended claims.

We claim:

1. A process for removing oxygen from a fluid stream containing oxygen and at least one other component, said process comprising bringing said fluid stream into contact with a solid state composition comprising one or more cyanocobaltate complexes comprising a cobalt-(II)-containing anion having from 3 to 5 cyanide ligands wherein at least one cyanide stretching mode, as measured by infrared spectroscopy, is between 2074 cm$^{-1}$ and 2140 cm$^{-1}$, and which complex further comprises a charge-balancing cation having a molecular volume in excess of 40Å$^3$, such that said complex selectively and reversibly binds oxygen thereby removing oxygen from the fluid stream.

2. The process of claim 1 wherein the complex contains a charge-balancing cation having a molecular volume in excess of 70Å$^3$.

3. The process of claim 1 wherein said cyanocobaltate complexes are represented by the chemical formula:

$$[c]^{z+}[Co(CN)_n]^{x-} \cdot pS\ x/z$$

where:
c is a cation
z is 1, 2 or 3:
n is any number from 3 to 5;
x is n-2;
p is any number from 0 to 6; and
S is a ligand which is capable of coordinating with $[c]^{z+}$, Co or both.

4. The process of claim 3 wherein S is selected from the group consisting of CN$^-$, N,N-dialkyl amides, alkyl lactams, N-alkyl imides, ammonia, acetone, chelating tertiary amines, N-heterocycles, organic nitriles, polymers containing polyvinylpyridine or pyrrolidone, cyanamide anion, dicyanamide anion, dicyanomethane anion, halide ions, SCN$^-$, NCS$^-$, and mixtures thereof.

5. The process of claim 3 wherein c is represented by the formula:

$$[(A)_a(R_4N)_b]$$

where:
A is alkali metal atom, alkaline earth metal atom, Zn, Cd or Hg atom;
a is any number from 0 to 3;
each R is independently C$_1$-C$_{10}$ substituted or unsubstituted alkyl, aryl or aralkyl; or a long chain hydrocarbon polymer:
b is any number from 0 to 2.5, with the proviso that both a and b cannot be zero.

6. The process of claim 3 wherein p is zero.

7. The process of claim 5 wherein p is zero.

8. The process of claim 6 wherein n is 5.

9. The process of claim 7 wherein R is a butyl group.

10. The process of claim 7 wherein "a" is zero.

11. The process of claim 7 wherein R is an ethyl group, butyl group, or a benzyl group.

12. The process of claim 7 wherein b is zero.

13. The process of claim 7 wherein A is Li, Na, Mg or Zn.

14. The process of claim 1 wherein said cyanocobaltate complex is (Et$_4$N)$_{0.5}$(Ph$_3$Sn)$_{2.5}$[Co(CN)$_5$].

15. The process of claim 1 wherein oxygen is selectively removed from a gas stream containing oxygen and nitrogen.

16. The process of claim 1 wherein oxygen is selectively removed from a gas stream containing argon and trace amounts of oxygen.

17. The process of claim 1 which is a pressure swing adsorption process.

18. The process of claim 1 which is a temperature swing adsorption process.

* * * * *